United States Patent
Bouchez et al.

(10) Patent No.: US 6,323,352 B1
(45) Date of Patent: Nov. 27, 2001

(54) POLYGLYCIDYL AZIDES COMPRISING AN ACYLOXY TERMINAL GROUP AND AN AZIDE TERMINAL GROUP

(75) Inventors: Jean-Marc Bouchez, Ballancourt sur Essone; Hervé Graindorge, Vert le Petit; Claude Soriaux, Mennecy, all of (FR)

(73) Assignee: SNPE, Paris Cedex (FR)

( * ) Notice: Subject to any disclaimer, the term of this patent is extended or adjusted under 35 U.S.C. 154(b) by 0 days.

(21) Appl. No.: 09/669,470

(22) Filed: Sep. 25, 2000

(30) Foreign Application Priority Data

Oct. 15, 1999 (FR) .................................................. 99 12865

(51) Int. Cl.⁷ ........................... C07C 247/00; C07J 41/00
(52) U.S. Cl. ............................................. 552/12; 560/155
(58) Field of Search ................................. 552/12; 560/155

(56) References Cited

U.S. PATENT DOCUMENTS 4,879,419 * 11/1989 Johanenssen et al. .
5,164,521 * 11/1992 Manzara et al. .

OTHER PUBLICATIONS

Loudon, GM, Organic Chemistry, third edition, 1995.*

* cited by examiner

Primary Examiner—Gary Geist
Assistant Examiner—Hector M Reyes
(74) Attorney, Agent, or Firm—Bucknam and Archer

(57) ABSTRACT

A subject-matter of the present invention is novel polyglycidyl azides of general formula (I):

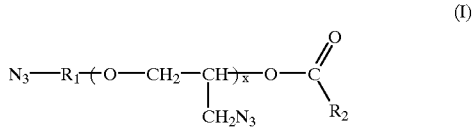

(I)

in which:

$R_1$ represents an alkylene chain comprising 2 to 4 carbon atoms, $R_2$ represents an alkyl chain comprising 1 to 4 carbon atoms, x represents an integer such that $4 \leq x \leq 10$.

These compounds are not detonatable and are of use in particular as energetic plasticizers in solid pyrotechnic compositions.

They can be obtained according to a 3-stage process starting from epichlorohydrin by preliminary synthesis of poly-epichlorohydrin with a hydroxyl terminal group of formula (II):

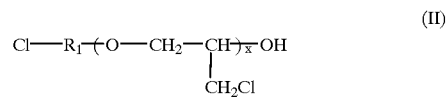

(II)

then acylation of this compound in order to obtain a poly-epichlorohydrin with an acyloxy terminal group of formula (IV):

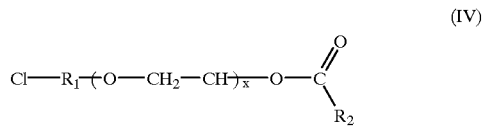

(IV)

and then azidation of this compound.

3 Claims, No Drawings

POLYGLYCIDYL AZIDES COMPRISING AN ACYLOXY TERMINAL GROUP AND AN AZIDE TERMINAL GROUP

The present invention relates to the field of solid pyrotechnic compositions, in particular that of solid propellants, composite explosives and firearm propellant powders.

A subject-matter of the invention is more specifically novel energetic plasticizers which can be used in the above mentioned solid pyrotechnic compositions.

These pyrotechnic compositions are generally obtained by pouring into a mould and then crosslinking a paste composed essentially of a crosslinkable binder, of a system for crosslinking this binder and of oxidizing and/or reducing charges.

Plasticizers are often incorporated in order to improve the use and the mechanical properties of the finished product, in particular at low temperatures. These plasticizers are preferably energetic compounds which are miscible but unreactive with the other constituents of the paste, in particular with the binder and the crosslinking agent.

The use is known, for this purpose, of alcohol nitrates, such as nitroglycerine and ethylene glycol dinitrate, but these compounds are particularly sensitive, detonatable and dangerous to handle.

Patent FR 2,707,979 furthermore discloses polyglycidyl azides (PGAs) terminated by azide functional groups which can be used as energetic plasticizers in such pyrotechnic compositions but it proves to be the case that these PGAs are also detonatable and that they have to be classified in category 1-1 according to Article 4 of the Interministerial Order of Sept. 26, 1980 relating to the classification of explosive substances (publication in the Official Gazette of the French Republic on Oct. 2, 1980) and the Interministerial Directive for implementation of this Order dated May 8, 1981, that is to say in a category corresponding to particularly sensitive products, such as hexogen, octogen and nitroglycerine, with all the constraints which this results in relating to safety of transportation, of storage and of use and thus with regard to the costs, which are consequently high.

U.S. Pat. No. 4,970,326 discloses PGA diacetates which can be used as plasticizers in solid pyrotechnic compositions but these compounds, which are certainly not detonatable, are markedly less energetic (nitrogen content of the order of 32–33%) than PGAs with azide terminal groups.

A person skilled in the art, who is constantly concerned about improving the safety of the processes and reducing the manufacturing costs, is therefore looking for novel energetic plasticizers entailing fewer pyrotechnic risks than the PGAs with azide terminal groups of the state of the art, in particular plasticizers which would be both energetic and nondetonatable.

A subject-matter of the present invention is such plasticizers, more specifically novel energetic polyglycidyl azides (nitrogen content in the region of 41%), which are liquid under standard temperature and pressure conditions, which can be used as energetic plasticizers in solid pyrotechnic compositions and which are nondetonatable, that is to say that they are classified in particular in category 1-3 according to the above mentioned Interministerial Order, that is to say in a category corresponding to products with reduced risks, such as firearm powders and propellants, and not in category 1-1, such as the detonatable PGAs disclosed in FR 2,707,979.

The novel polyglycidyl azides according to the invention correspond to the general formula (I)

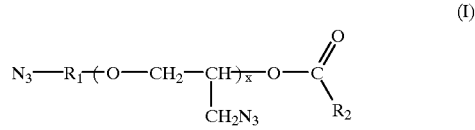

in which:

R$_1$ represents an alkylene chain comprising 2 to 4 carbon atoms, preferably —(CH$_2$)$_2$—, R$_2$ represents an alkyl chain comprising 1 to 4 carbon atoms, preferably —CH$_3$, x represents an integer such that $4 \leq x \leq 10$, preferably such that $6 \leq x \leq 8$.

These novel PGAs of formula (I) according to the invention can be obtained in 3 stages from epichlorohydrin.

In a first stage, a polyepichlorohydrin with a hydroxyl terminal group of general formula (II)

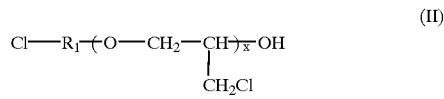

in which x and R$_1$ have the above mentioned meanings, is synthesized by polymerization, generally in an organic solvent medium, preferably a halogenated organic solvent medium, of epichlorohydrin in the presence of an initiating alcohol of general formula Cl—R$_1$—OH (III), in which R$_1$ has the above mentioned meaning.

Such a reaction is well known to a person skilled in the art and is generally carried out in the presence of a catalyst of Lewis acid type, for example a BF$_3$ etherate.

In a second stage, a polyepichlorohydrin with an acyloxy terminal group of general formula (IV)

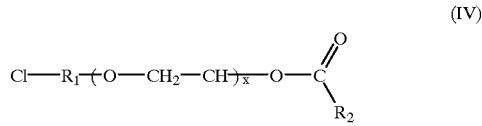

in which R$_1$, R$_2$ and x have the above mentioned meanings, is synthesized by reaction, in the presence of a basic organic catalyst, of the above mentioned polyepichlorohydrin with a hydroxyl terminal group of formula (II) with an acylating agent of general formula

in which R$_2$ has the above mentioned meaning and Z represents a hydroxyl, halide (preferably Cl or Br) or acyloxy group.

In a particularly preferred way, the acylating agent of formula (V) is an anhydride of formula

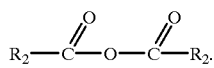

The acylating agent is generally used in a very large molar excess with respect to the hydroxyl functional groups. It is possible, for example, to use a molar ratio of between 2 and 8.

The basic organic catalyst is preferably chosen from the group consisting of pyridines and imidazoles. Pyridine and 1-methylimidazole are particularly preferred.

Mention may be made, as examples of other suitable catalysts, of trialkylamines, in particular triethylamine.

The amount of catalyst generally used is between 10 mol % and 50 mol % with respect to the hydroxyl functional groups to be esterified.

According to a preferred alternative form, this second stage is carried out in an organic solvent medium, preferably a halogenated organic solvent medium, more particularly a chlorinated organic solvent medium, such as $CHCl_3$, $CCl_4$, $CH_2Cl_2$ and $CH_2Cl—CH_2Cl$.

The temperature of this acylation reaction is preferably between 40° C. and 100° C. The temperature range 70° C.–90° C. is particularly preferred and the reaction is preferably carried out at reflux of the solvent.

After reacting the polyepichlorohydrin with a hydroxyl terminal group of formula (II) with the acylating agent of formula (V), the polyepichlorohydrin with an acyloxy terminal group of general formula (IV) formed is isolated from the reaction mixture and then identified according to conventional physical, chemical, chromatographic and spectrometric analytical methods.

Infrared spectrometry shows in particular, in comparison with the spectrum of the starting polyepichlorohydrin with a hydroxyl terminal group, the disappearance of the hydroxyl bands and the appearance of a carbonyl band, while the C—Cl band is still present.

In a third stage, an azidation is carried out on the chloride functional groups of the above mentioned polyepichlorohydrin with an acyloxy terminal group of general formula (IV) obtained in the second stage, preferably by means of an alkali metal azide.

It has been found, in a particularly unexpected way, that the acyl functional group carried by the intermediate polyepichlorohydrins of general formula (IV) is inert with regard to the azidation reactants and that it is therefore not, even partially, converted to an azide functional group, whereas the state of the art and in particular the above mentioned U.S. Pat. No. 4,970,329 prompts a person skilled in the art to carry out the azidation reaction before the acylation reaction, with the disadvantages which result therefrom with regard to safety (greater number of pyrotechnic stages) and therefore with regard to costs.

According to the invention, only the third and last stage is a pyrotechnic stage, which significantly limits the pyrotechnic risks and the overall cost.

According to a preferred alternative form, this third azidation stage is carried out by means of an alkali metal azide, for example $NaN_3$.

According to another preferred alternative form, this azidation stage is carried out in an organic solvent medium, preferably a polar organic solvent medium, such as dimethyl sulphoxide (DMSO) and dimethylformamide (DMF).

The temperature of the azidation reaction is preferably between 70° C. and 110° C., more particularly between 90° C. and 100° C.

After the reaction, followed by cooling of the reaction mixture, the novel PGAs of formula (I) according to the invention can be isolated from the mixture, for example by precipitation by adding water to the mixture, and then purified by dissolution in a chlorinated solvent, such as methylene chloride, followed by drying, filtration and evaporation of the solvent.

The purified product can subsequently be identified according to conventional physical, chemical, chromatographic and spectrometric analytical methods.

Infrared spectrometry shows in particular, in comparison with the spectrum of the starting polyepichlorohydrin with an acyloxy terminal group, the appearance of the bands characteristic of the C—$N_3$ bond and the disappearance of the C—Cl band, while the carbonyl band is still present.

Another subject-matter of the present invention, in addition to the above mentioned novel PGAs of formula (I), is any solid pyrotechnic composition, in particular any solid propellant, any composite explosive and any firearm propellant powder, comprising an above mentioned polyglycidyl azide of formula (I) and any use of such a PGA as energetic plasticizer in the said solid pyrotechnic compositions.

The following nonlimiting examples illustrate the invention and the advantages which it provides.

EXAMPLE 1

Preparation of a polyepichlorohydrin with a hydroxyl terminal group of formula (II) with $R_1$=—$(CH_2)_2$—.

380 g of 1,2-dichloroethane (solvent), 62.85 g (0.78 mol) of 2-chloroethanol (initiator) and 5.35 g ($3.8 \times 10^{-2}$ mol) of boron trifluoride etherate (catalyst) are introduced into a 500 ml jacketed reactor equipped with a mechanical stirrer, a temperature probe and a water-cooled reflux condenser.

The mixture is brought to 30° C. and then 650 g (7.03 mol) of epichlorohydrin are added dropwise over 6 hours while maintaining the temperature at 30° C.

After the reaction, the reaction mixture is poured into 0.75 l of water comprising 15 g of $K_2CO_3$.

After stirring for approximately 20 min and then separating by settling, the aqueous phase is removed and then the organic phase is washed a second time with water to which $K_2CO_3$ has been added and then a third time with pure water.

After evaporating the solvent, 685 g (96% yield) of a colourless liquid are collected, for which the main characteristics measured are as follows:

Hydroxyl level: 1.11 eq OH/kg

Analysis by gel permeation chromatography with PPG calibration:

$\overline{Mn}$=700

$\overline{Mw}$=800

$$I = \frac{\overline{Mw}}{\overline{Mn}} = 1.15$$

IR spectrum in agreement with the formula (II) with in particular the presence of an OH band at 3472 $cm^{-1}$ and a C—Cl band at 747 $cm^{-1}$.

EXAMPLE 2

Preparation of a polyepichlorohydrin with an acetyloxy terminal group of formula (IV) with $R_1$=—$(CH_2)_2$— and $R_2$=—$CH_3$.

200 g of the polyepichlorohydrin with a hydroxyl terminal group obtained according to Example 1 are dissolved in 300 ml of 1,2-dichloroethane in a 1 l jacketed reactor equipped with a mechanical stirrer, a temperature probe and a water-cooled reflux condenser and then 120 g (1.18 mol) of acetic anhydride are added at room temperature (approximately 18° C.).

10 ml (0.125 mol) of 1-methylimidazole are subsequently added, the reaction mixture is then brought to reflux of the 1,2-dichloroethane (81° C.) and this temperature is maintained for 3 h.

After cooling to room temperature, the mixture is washed with 300 ml of water and is then dried over magnesium sulphate.

After filtration and then evaporation of the solvent, 170 g (81% yield) of a colourless liquid are recovered, the IR spectrum of which liquid exhibits a carbonyl band at 1743 cm$^{-1}$ and a C—Cl band at 747 cm$^{-1}$ but does not exhibit a hydroxyl band.

EXAMPLE 3

Preparation of a polyglycidyl azide with an acetyloxy terminal group of formula (I) according to the invention with $R_1$=—$(CH_2)_2$— and $R_2$=—$CH_3$.

340 ml of DMSO and 170 g of the polyepichlorohydrin with an acetate terminal group obtained according to Example 2 are introduced into a 1 l jacketed reactor equipped with a mechanical stirrer, a temperature probe and a water-cooled reflux condenser.

The temperature of the mixture is brought to approximately 75° C., 139.6 g (2.15 mol) of sodium azide are then introduced portionwise, so as to maintain the temperature of the reaction mixture between 90 and 95° C., and then the temperature of the mixture is maintained at 95° C. for 24 h.

After cooling to room temperature, 500 ml of water are added. A product precipitates, which product is collected by filtration, then washed with 3 times 500 ml of water in order to remove the residual DMSO and then dissolved in 500 ml of methylene chloride.

After drying over magnesium sulphate, followed by filtration and then evaporation of the solvent, 163 g (90% yield) of a yellowish oil are collected, for which the main characteristics measured are as follows:

IR spectrum in agreement with the formula (I) with in particular the presence of bands at 1282 cm$^{-1}$, 2101 cm$^{-1}$, 2520 cm$^{-1}$ and 3362 cm$^{-1}$ characteristic of the C—$N_3$ bond and of a carbonyl band at 1743 cm$^{-1}$. This spectrum does not exhibit a hydroxyl band or a band characteristic of the C—Cl bond at 747 cm$^{-1}$.

Analysis by gel permeation chromatography with PPG calibration:

$\overline{Mn}$=740

$\overline{Mw}$=850

$$I = \frac{\overline{Mw}}{\overline{Mn}} = 1.15$$

Nitrogen content: 41.1%

Density at 20° C.: 1.269 g/cm$^3$

Residual chlorine level: <0.2%

Residual water level: 0.05%

Residual DMSO level: 0.1%

Sensitivity to impact at 20° C. and 40° C. (Julius Peters device): absence of detonation at 50 J (30 tests at each temperature)

Stability under vacuum (100° C., 193 h): 2.8 cm$^3$/g

Classification tests according to the above mentioned Interministerial Order and the above mentioned Implementational Directive: classification in category 1-3.

By way of comparison, these same tests were carried out on a sample of PGA such as that disclosed in FR 2,707,979. The results show that such a PGA has to be classified in category 1-1.

What is claimed is:

1. Polyglycidyl azides of general formula (I)

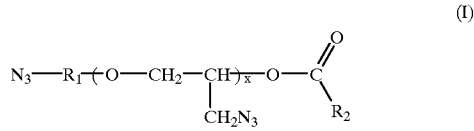

in which:

$R_1$ represents an alkylene chain comprising 2 to 4 carbon atoms, $R_2$ represents an alkyl chain comprising 1 to 4 carbon atoms, x represents an integer such that $4 \leq x \leq 10$.

2. Polyglycidyl azides according to claim 1, characterized in that $R_1$ represents —$(CH_2)_2$— and $R_2$ represents —$CH_3$.

3. Polyglycidyl azides according to claim 1, characterized in that x is such that $6 \leq x \leq 8$.

* * * * *